(12) United States Patent
Weil et al.

(10) Patent No.: US 7,037,309 B2
(45) Date of Patent: May 2, 2006

(54) SELF-TAPPING SCREW FOR SMALL-BONE SURGERY

(75) Inventors: Lowell Scott Weil, Des Plaines, IL (US); Louis Samuel Barouk, La Manchotte 39, Chemin de la Roche - 33370, Yvrac (FR); Thierry Souillat, Villemontais (FR)

(73) Assignees: Depuy (Ireland) Limted, County Cork (IE); Louis Samuel Barouk, Yvrac (FR)

( * ) Notice: Subject to any disclaimer, the term of this patent is extended or adjusted under 35 U.S.C. 154(b) by 540 days.

(21) Appl. No.: 10/186,630

(22) Filed: Jul. 2, 2002

(65) Prior Publication Data

US 2003/0028193 A1 Feb. 6, 2003

Related U.S. Application Data

(60) Provisional application No. 60/302,671, filed on Jul. 5, 2001.

(51) Int. Cl.
*A61B 17/58* (2006.01)

(52) U.S. Cl. .......................................... 606/73; 606/72

(58) Field of Classification Search ................. 606/59, 606/64, 65, 54, 57, 70–73, 76, 104, 215, 606/216, 232, 69, 213; 411/389, 397, 395, 411/413

See application file for complete search history.

(56) References Cited

U.S. PATENT DOCUMENTS

| | | | | |
|---|---|---|---|---|
| 4,175,555 A | * | 11/1979 | Herbert | 606/73 |
| 4,463,753 A | * | 8/1984 | Gustilo | 606/73 |
| 4,537,185 A | * | 8/1985 | Stednitz | 606/73 |
| 4,858,601 A | * | 8/1989 | Glisson | 606/73 |
| 5,019,079 A | * | 5/1991 | Ross | 606/72 |
| 5,300,076 A | * | 4/1994 | Leriche | 606/73 |
| 5,334,204 A | * | 8/1994 | Clewett et al. | 606/73 |
| 6,001,101 A | | 12/1999 | Augagneur et al. | |
| 6,030,162 A | * | 2/2000 | Huebner | 411/413 |

FOREIGN PATENT DOCUMENTS

FR 2 722 086 A1 1/1996

* cited by examiner

*Primary Examiner*—Anhtuan T. Nguyen
(74) *Attorney, Agent, or Firm*—Young & Thompson

(57) ABSTRACT

Self-tapping screw for small-bone surgery, includes a threaded proximal head (2), a threaded distal shank with greater pitch and an internal cannula (4), characterized in that the distal shank (3) is threaded over its entire length in that the end of the shank has, apart from milled portions forming self-tapping faces on the first distal threads, at least two milled faces and which with the cannula, determine at least two notches (11), and at least two self-boring edges at the distal end of the screw, and in that the thread of the head has, aside from milled portions forming self-tapping faces on the first threads of the proximal screw thread, chamfered faces (16–19), determining boring edges (12b–15b) preceded by a short groove.

15 Claims, 3 Drawing Sheets

SELF-TAPPING SCREW FOR SMALL-BONE SURGERY

BACKGROUND OF THE INVENTION

The subject of the present invention is a self-tapping screw for small-bone surgery, particularly on the foot.

DESCRIPTION OF THE RELATED ART

It is known that in small-bone surgery, use is made of screws such as the screw known as the Barouk screw which comprises a threaded proximal head and a threaded distal shank. The screw thread of the head has a smaller pitch than that of the distal part so as to make the screw self-compressing, that is to say screwing it in causes compression of the two bits of bone that are to be osteosynthesized by virtue of the difference between the pitches of the two screw threads. This screw also has a cannula and is self-tapping by virtue of notches made on the screw threads of the head and of the end of the distal shank. Finally, the diameter of the screw thread of the head is greater than the diameter of the screw thread of the distal part.

Screws of this kind are generally made of titanium.

The Barouk screw has a short plain intermediate zone between the threaded head and the start of the threaded distal part. This plain zone, which has a diameter identical to that of the distal screw thread, normally lies on each side of the osteotomy line and therefore allows the two bits of bone to be compressed one against the other without damaging the bony wall of the borehole, as the threaded distal part finishes entering the bone.

French application FR-A-2722086 describes a similar screw in which this intermediate portion, the diameter of which is slightly smaller than that of the distal screw thread, can be of shorter length or almost absent. This screw does, however, require the prior boring of a hole, with diameters similar to the root diameters of the distal and proximal threads, using a drill bit, the screw threads of the screw then performing their self-tapping function.

SUMMARY OF THE INVENTION

It is an object of the invention to provide a screw which does not have these disadvantages and which, at least in certain cases, allows the screw to be screwed in without the prior boring of a hole with the thread root diameter.

Another objective of the invention is to provide a screw of this type which performs particularly well as regards self-tapping and self-boring.

Yet another objective is to provide sets of screws which are particularly suited to fitting the screws which are best suited to each particular case.

According to the invention, the self-tapping screw is characterized in that the distal shank is threaded over its entire length to meet the threaded head, in that the screw has an internal passage in the manner of a cannula, in that the distal end of the distal shank has, apart from the self-tapping milled portions on the first distal threads, at least two milled portions which are angularly equidistant about the longitudinal axis of the screw and such that they, with the cannula-type passage, determine at least two notches in the end of this passage and at least two self-boring edges at the distal end of the screw, and in that the distal end of the screw thread of the head has, aside from the self-tapping milled portions on the first threads of the proximal screw thread, angularly equidistant chamfered milled portions determining boring edges which open into a short relief groove which follows the distal screw thread.

As a preference, the dimensions of the screw according to the invention lie in the following ranges:
screw length: 10 mm to 60 mm
head length 5–10 mm
pitch of distal screw thread: between 1 and 3 mm
pitch of proximal screw thread: between 0.8 and 2.5 mm
diameter of the distal part (crest of thread): 2.5 to 5 mm.

Another subject of the invention is a set of several of these screws having different dimensions, and, in accordance with a particularly preferred feature, such a set contains a number of screws of different lengths, but having the same characteristics in terms of diameter and therefore diametral size and self-boring and self-tapping ability.

DESCRIPTION OF THE PREFERRED EMBODIMENTS

Figure 1:
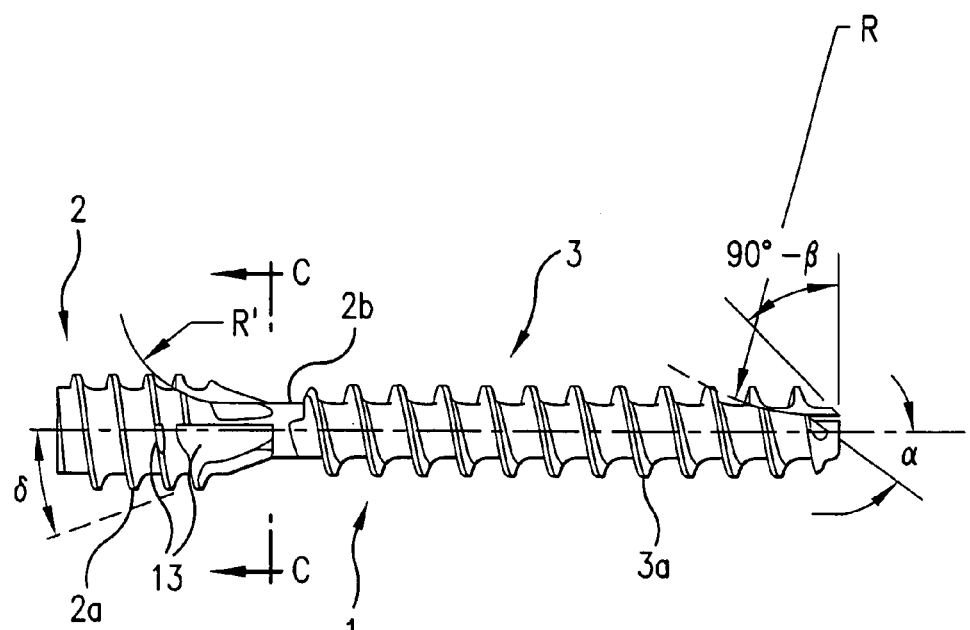
FIG. 1 depicts a view in elevation of a screw according to the invention.
Figure 2:
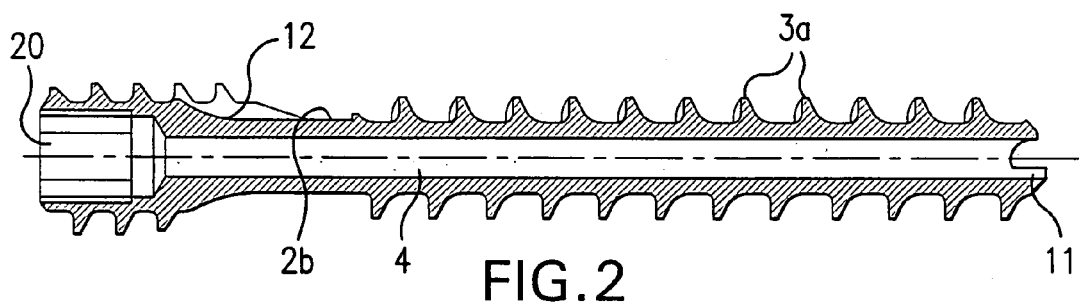
FIG. 2 depicts a view in axial section of this screw.
Figure 3:
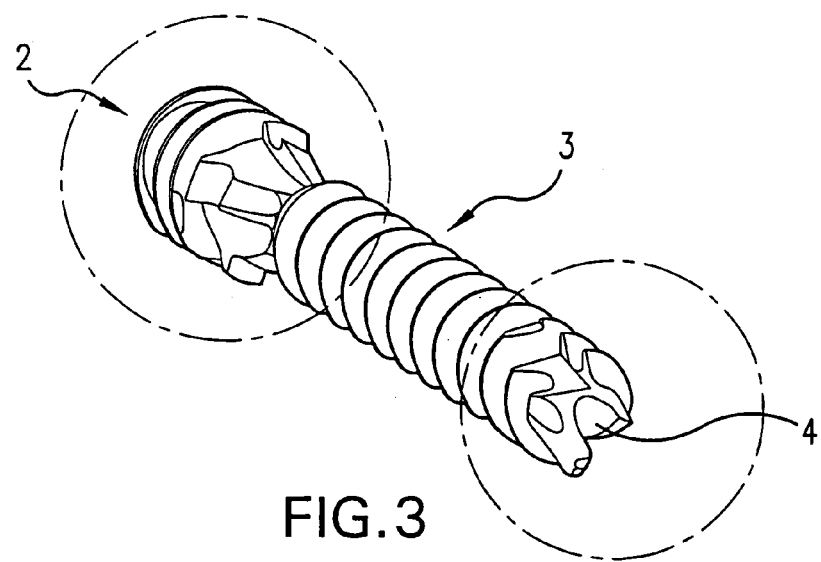
FIG. 3 depicts a perspective view of this screw.
Figure 4:
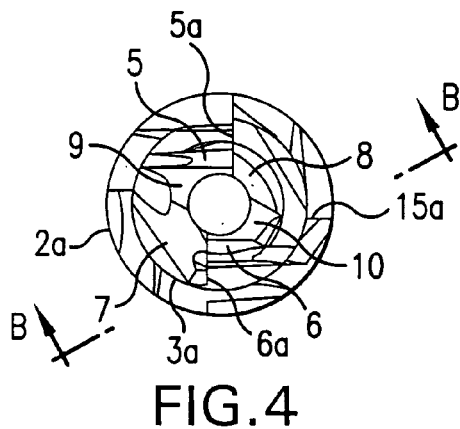
FIG. 4 depicts a view of the distal end of the screw.
Figure 5:
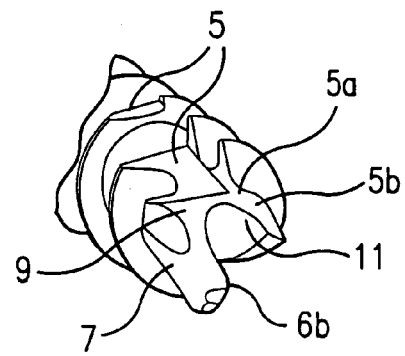
FIG. 5 depicts a perspective view of this distal end.
Figure 6:
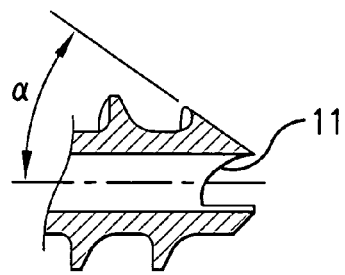
FIG. 6 depicts an enlarged view of this anterior end, in axial section B—B of FIG. 4.
Figure 7:
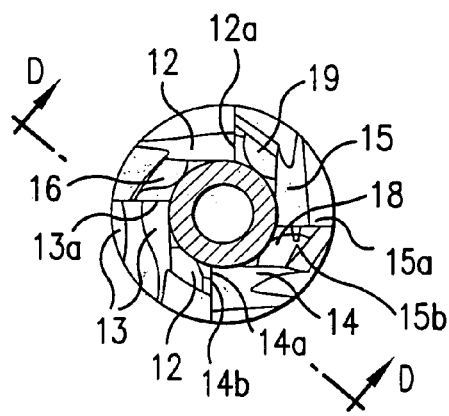
FIG. 7 depicts a view in cross section C—C of FIG. 1 of the screw just before the part which forms the screw head.

The screw illustrated in FIG. 1 is intended for small-bone surgery, particularly on the foot.

This screw 1 comprises a threaded proximal head 2 and a threaded distal shank 3. The distal shank 3 is threaded over its entire length and is connected directly to the threaded head 2 by a short relief groove 2b so that there is no plain intermediate portion between the head 2 and the distal shank 3.

An axial canal 4 is formed throughout the length of the screw 1 at the ends of which it opens freely. In the head 2 the canal 4 opens into a hexagonal socket 20 shaped to take the end of a screwing tool, not depicted, the canal 4 and the socket 20 being coaxial with the overall longitudinal axis of the screw 1. The diameter of the head 2 is appreciably greater than the diameter of the distal shank 3 and the screw thread 2a of the head 2 has a pitch which is shorter than the pitch of the screw thread 3a of the distal shank 3.

It will therefore be understood that the screw essentially has two parts, namely a longer distal part with a cylindrical screw thread which has a first pitch, and a head part with a screw thread of larger diameter and which has a pitch shorter than that of the distal part.

The proximal head 2 at its anterior end has the said short groove 2b into which the self-boring means of the head 3 open.

As a preference, the anterior flanks of the screw threads, that is to say the flanks facing towards the distal end, of the screw threads are inclined forward while the posterior flanks are practically perpendicular to the axis of the screw.

The same is preferably true of the threads 2a.

According to the invention, two angularly equidistant milled portions are made at the distal end of the part of the distal screw thread 3. These milled portions are obtained as follows:

Initially, for example before producing the screw threads, the distal end of the screw is conical with a cone angle β with respect to the longitudinal axis of the screw. The thread turning operations are then carried out to produce the screw threads 2a, 3a of the distal and proximal parts, these screw threads having different pitches as specified hereinabove.

Two passes of a milling cutter of radius R are then made on the distal end, that is to say the free end, of the distal part 3, each pass being offset from the other by 180° about the longitudinal geometric axis of the screw. FIG. 1 shows that this pass intersects the first two threads of the screw and makes a very slight impact on the crest of the third thread. The radius R of the milling cutter and the position of the center of the milling cutter are such that the faces 5 or 6 obtained do not intersect the internal passage 4 but remain slightly outside. These milled portions also form two faces 5a, 6a perpendicular to the faces 5 and 6 and parallel to the axis of the screw, and thus determine the self-tapping sections of the first threads.

Two flat milled portions inclined by α with respect to the axis are also made, in the continuation of the previous milled portions, these two flat milled portions forming faces 9 and 10 which intersect the internal surface of the cannula-type hole 4 to form notches 11. The milled portions which form the faces 9 and 10 also form perpendicular faces which form the exact distal continuations of the faces 5a, 6a.

Next, having turned the screw, two milled portions are produced which determine faces 7 and 8, which are also inclined with respect to the geometric axis of the screw. The intersections between the faces 8, 5a and, respectively, 7, 6a form, at the distal end, two small self-boring cutting edges 5b, 6b.

It is thus possible to achieve self-tapping and a certain amount of self-boring into the bone tissue, as the screw progresses. The self-boring abilities afforded by the edges are sufficient, at least for certain types of bone, to be able to dispense with the prior borehole, this being particularly true of screws according to the invention which have the smallest diameters.

Figure 8:
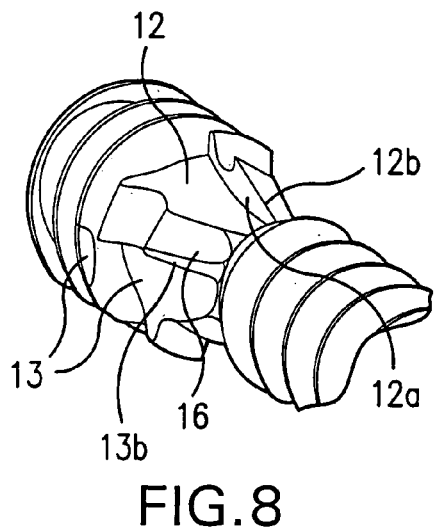
FIG. 8 depicts a perspective view of the screw head part.
Figure 9:
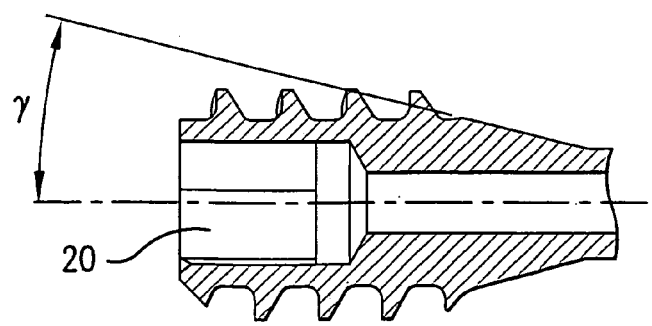
FIG. 9 depicts a view in diametral section D—D of this head part.
Figure 10:
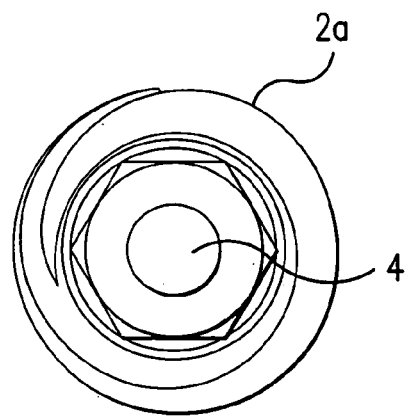
FIG. 10 depicts a view of the proximal end of the screw.
Figure 11:
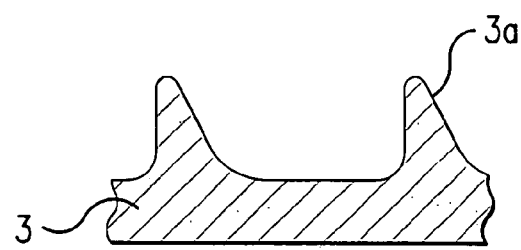
FIG. 11 depicts an enlarged diametral section of the screw thread of the distal part of the screw.
Figure 12:
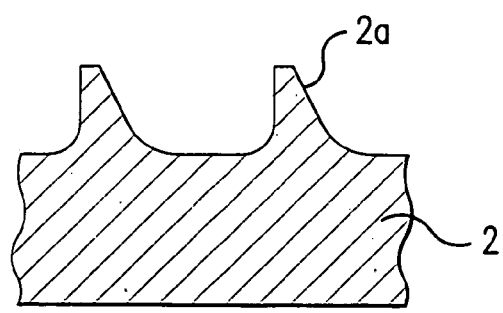
FIG. 12 depicts an enlarged sectional view of a part of the screw thread of the screw head.

In order to give the screw thread 2a of the proximal head 2, which initially has a conical part of inclination γ which narrows toward the groove 2b, a self-tapping end, four milled portions angularly offset by 90° are produced using a milling cutter of radius R'. The passes roughly intersect two threads, as can be seen in FIGS. 1 and 8 and thus determine faces 12, 13, 14, 15 with their perpendicular tapping faces 12a, 13a, 14a, 15a, these faces being supplemented by four flat milled portions of inclination δ with respect to the axis of the screw, as can be seen in particular in FIGS. 8 and 9, to form faces 16, 17, 18, 19, of which the edges formed with the faces 12a to 15a constitute cutting edges 12b to 15b allowing self-boring action.

It will be understood that the head 2, via its self-boring edges which end practically at the groove 2b, will perform a certain amount of self-boring which begins in the bone threads tapped by the distal threaded part 3, then ends when the self-tapping sections of the threads, which sections are determined by the milled portions 12, 13, 14, 15, come into action.

There has thus been produced a screw which has improved qualities in terms of self-tapping, self-boring and screwing, then in terms of compressively holding the two bits of bone fragments, for example of metatarsus, together.

The invention is not restricted to the various forms of embodiment described and may involve various embodiment variants.

The invention claimed is:

1. Self-tapping screw for small-bone surgery, particularly of the Barouk screw type, comprising:
   a threaded proximal head (2) with a screw thread;
   a threaded distal shank (3) with a screw thread,
   the pitch of the screw thread on the proximal head being shorter than the pitch of the screw thread of the distal shank; and
   an internal passage (4) in the manner of a cannula,
   the distal shank (3) threaded over its entire length to meet the threaded head (2),
   the distal end of the distal shank having milled portions forming angularly equidistant self-tapping faces (5, 5a, 6, 6a) on first distal threads terminating portions of the screw thread of the distal shank,
   apart from the milled portions, at least two milled portions forming angularly equidistant faces (9, 10) about the longitudinal axis of the screw that together with the internal passage determine at least two notches (11) in the terminal end of the internal passage,
   at least two self-boring cutting edges (5b, 6b) at the distal end of the screw,
   the distal end of the screw thread of the head having first milled portions forming angularly equidistant self-tapping faces (12 to 15, 12a to 15a) on first threads of the proximal screw thread,
   aside the first milled portions, second milled portions forming angularly equidistant chamfered faces (16–19), the second milled portions determining boring edges (12b–15b); and
   a short groove (2b) preceding the boring edges and following the screw thread of the distal shank.

2. Screw according to claim 1, characterized,
   in that the milled portions forming angularly equidistant self-tapping faces (5, 6) are preceded by the milled portions (9, 10) determining the notches (11) and also forming respectively common perpendicular faces (5a, 6a), and
   in that angularly offset milled portions (7, 8) determine, with said perpendicular faces (5a, 6a) said cutting edges (5b, 6b).

3. Screw according to claim 1, characterized by dimensions which lie in the following ranges:
   screw length: 10 mm to 60 mm
   head length 5–10 mm
   pitch of distal screw thread: between 1 and 3 mm
   pitch of proximal screw thread: between 0.8 and 2.5 mm
   diameter of the distal part (crest of thread): 2.5 to 5 mm.

4. Set of several screws according to claim 1, having different dimensions.

5. Set according to claim 4, characterized in that it contains a number of screws of different lengths, but having the same characteristics in terms of diameter and therefore diametral size and self-boring and self-tapping ability.

6. Self-tapping screw for small-bone surgery, particularly of the Barouk screw type, comprising:
   a threaded proximal head (2) and a threaded distal shank (3), the pitch of the screw thread on the proximal head being shorter than the pitch of the screw thread on the distal shank, and an internal passage (4) in the manner of a cannula, wherein, the distal shank (3) is threaded over its entire length to meet the threaded head (2), the distal end of the distal shank has milled portions forming angularly equidistant self-tapping faces (5, 5a, 6, 6a) on first distal threads, at least two milled portions, preceding said self-tapping faces (5, 5a, 6, 6a) and forming angularly equidistant faces (9, 10) about the longitudinal axis of the screw and having respectively common perpendicular faces (5a, 6a) with the taping faces that with the internal passage, determine at least two notches (11) in the end of the internal passage, and angularly offset milled portions (7, 8) determine with said perpendicular faces (5a, 6a) at least two self-boring cutting edges (5b, 6b) at the distal end of the screw, and milled portions at the distal end of the screw thread of the head, and located aside from milled portions forming angularly equidistant self-tapping faces (12 to 15, 12a to 15a) on first threads of the proximal screw thread, form angularly equidistant chamfered faces (16–19), the chamfered faces determining boring edges (12b–15b), and the milled portions are preceded by a short groove (2b) which follows the distal screw thread.

7. Screw according to claim 6 characterized by dimensions which lie in the following ranges:
screw length: 10 mm to 60 mm
head length 5–10 mm
pitch of distal screw thread: between 1 and 3 mm
pitch of proximal screw thread: between 0.8 and 2.5 mm
diameter of the distal part (crest of thread): 2.5 to 5 mm.

8. Set of several screws according to claim 6, having different dimensions.

9. Set according to claim 8, characterized in that it contains a number of screws of different lengths, but having the same characteristics in terms of diameter and therefore diametral size and self-boring and self-tapping ability.

10. A self-tapping surgery screw, comprising:
a threaded proximal head (2);
a threaded distal shank (3), the shank threaded over the entire overall length thereof;
a relief groove (2b) directly connecting the head to the shank, a maximum diameter of the relief groove being less than a maximum diameter of the shank;
an axial canal (4) formed throughout the entire overall length of the head, relief groove, and the shank;
a socket (20) in the head, the socket shaped to take a screwing tool end;
a first self-boring part located at the terminal end of the shank and including at least two self-boring cutting edges (5b, 6b) at the distal end of the shank, and at least two milled portions forming angularly equidistant faces (9, 10) about the longitudinal axis of the shank that together with the axial canal define at least two notches (11) in the terminal end of the axial canal; and
a second self-boring part located at an end of the head adjacent the relief groove and opening to the relief groove.

11. The screw of claim 10, wherein,
the distal end of screw threads of the head have first milled portions forming angularly equidistant self-tapping faces (12 to 15, 12a to 15a) on the screw threads of the thread, and aside the first milled portions, second milled portions form angularly equidistant chamfered faces (16–19), the second milled portions determining boring edges (12b–15b) of the second self-boring part.

12. The screw of claim 10, wherein,
the shank is a longer distal part of the screw and has a cylindrical, first screw thread of a first pitch, and
the head has a second screw thread of larger diameter, as compared to the first screw thread, and a second pitch shorter than the first pitch.

13. The screw of claim 12, wherein,
screw threads facing towards the distal end have anterior flanks inclined forward and have posterior flanks practically perpendicular to the axis of the screw.

14. The screw of claim 13, wherein the screw threads of the head have anterior flanks inclined forward and have posterior flanks practically perpendicular to the axis of the screw.

15. The screw of claim 10, wherein,
the second self-boring part has an initial conical part of a first inclination ($\gamma$) narrowing toward the relief groove (2b), a self-tapping end, and four milled portions angularly offset by 90° defining four faces (12, 13, 14, 15) with perpendicular tapping faces (12a, 13a, 14a, 5a) supplemented by four flat milled portions of a second inclination ($\delta$) with respect to the axis of the screw.

\* \* \* \* \*